United States Patent
Addison et al.

(10) Patent No.: US 7,772,454 B2
(45) Date of Patent: Aug. 10, 2010

(54) WOUND TREATMENT DEVICE

(75) Inventors: Deborah Addison, Keasden (GB); Alicia J. Essler, Skipton (GB); Breda M. Cullen, Skipton (GB); Derek W. Silcock, Skipton (GB)

(73) Assignee: Systagenix Wound Management (U.S.), Inc., Wilmington, DE (US)

( * ) Notice: Subject to any disclaimer, the term of this patent is extended or adjusted under 35 U.S.C. 154(b) by 0 days.

(21) Appl. No.: 10/528,742

(22) PCT Filed: Sep. 25, 2003

(86) PCT No.: PCT/GB03/04118

§ 371 (c)(1),
(2), (4) Date: Oct. 6, 2005

(87) PCT Pub. No.: WO2004/028423

PCT Pub. Date: Apr. 8, 2004

(65) Prior Publication Data

US 2006/0111657 A1  May 25, 2006

Related U.S. Application Data

(60) Provisional application No. 60/486,445, filed on Jul. 14, 2003.

(30) Foreign Application Priority Data

Sep. 27, 2002 (GB) ................. 0222527.4

(51) Int. Cl.
*A61L 15/00* (2006.01)
*A61F 13/00* (2006.01)
*A61F 15/00* (2006.01)

(52) U.S. Cl. ............. 602/48; 602/41; 602/42; 602/43; 602/56; 602/58; 604/304; 424/445

(58) Field of Classification Search ............ 424/445; 602/46, 48, 41–43, 50, 56, 58; 604/304
See application file for complete search history.

(56) References Cited

U.S. PATENT DOCUMENTS

| | | | |
|---|---|---|---|
| 3,464,413 A | 9/1969 | Goldfarb et al. | |
| 3,886,084 A | 5/1975 | Vassiliades | |
| 4,499,896 A * | 2/1985 | Heinecke | 602/47 |
| 4,541,426 A | 9/1985 | Webster | |
| 4,898,734 A | 2/1990 | Mathiowitz et al. | |

(Continued)

FOREIGN PATENT DOCUMENTS

EP  0613692 B1  1/1999

(Continued)

*Primary Examiner*—Patricia M Bianco
*Assistant Examiner*—Brandon Jackson
(74) *Attorney, Agent, or Firm*—Morgan, Lewis & Bockius LLP

(57) ABSTRACT

A wound treatment device comprising a water-impermeable envelope having at least one aperture. The envelope contains a therapeutic substance. The at least one aperture in the envelope is blocked by a material that breaks down in the presence of one or more active components of wound fluid thereby permitting the therapeutic substance to contact the wound fluid. Preferably, the aperture is blocked by a material that is a substrate for an enzyme present in would fluid, such as a protease.

12 Claims, 1 Drawing Sheet

U.S. PATENT DOCUMENTS

Figure 1:
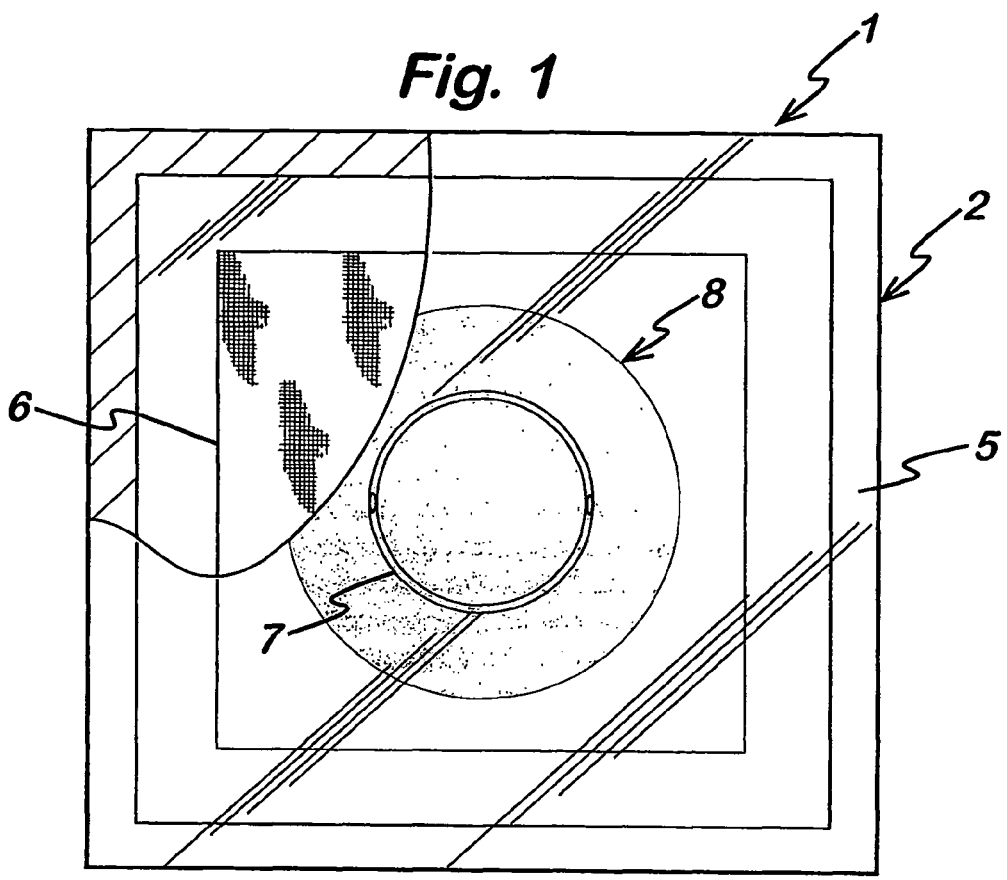

| | | |
|---|---|---|
| 5,352,508 A | 10/1994 | Cheong |
| 5,540,922 A | 7/1996 | Fabo |
| 5,549,908 A | 8/1996 | Smith et al. |
| 5,759,570 A * | 6/1998 | Arnold .................. 424/443 |
| 6,143,037 A | 11/2000 | Bonadio et al. |
| 6,153,215 A * | 11/2000 | Samuelsen et al. .......... 424/448 |
| 6,160,200 A * | 12/2000 | Ehrnsperger et al. ........ 604/378 |
| 6,903,243 B1 * | 6/2005 | Burton .................. 602/41 |
| 2004/0241214 A1 * | 12/2004 | Kirkwood et al. .......... 424/445 |
| 2005/0159695 A1 * | 7/2005 | Cullen et al. .................. 602/48 |
| 2006/0286155 A1 * | 12/2006 | Trotter et al. .................. 424/445 |

FOREIGN PATENT DOCUMENTS

| | | |
|---|---|---|
| EP | 0599589 B1 | 2/1999 |
| EP | 0875222 B1 | 7/2002 |
| GB | 2369997 A | 6/2002 |
| GB | 2392836 A | 3/2004 |
| WO | WO 96/10374 A1 | 4/1996 |
| WO | WO 02/38097 A1 | 5/2002 |
| WO | WO 03/026544 A | 4/2003 |

* cited by examiner

WOUND TREATMENT DEVICE

CROSS-REFRENCE TO RELATED APPLICATIONS

This application is a National Stage application under 35 U.S.C. 371 of PCT/GB2003/004118, filed 25 Sep. 2003, which claims priority from GB0222527.4 filed Sep. 27, 2002, and U.S. Provisional Application Ser. No. 60/486,445 filed Jul. 14, 2003.

The present invention relates to articles that can provide controlled delivery of one or more therapeutic agents to a wound.

The amount and composition of wound fluid (exudate) produced by a wound depends on the type of wound and the history of wound healing. For example, surgical wounds have an acute inflammatory phase of a few days during which discharge is significant, after which the rate of exudate production can be expected to fall sharply. Chronic wounds, such as ulcers, produce wound fluid containing elevated levels of protease enzymes. Infected wounds generally produce substantially more exudate than non-infected wounds, and the composition of the wound fluid is different. Burns produce large amounts of wound exudate having characteristic properties.

Infection of wounds by bacteria delays the healing process, since bacteria compete for nutrients and oxygen with macrophages and fibroblasts, whose activities are essential for the healing of the wound. Infection results when bacteria achieve dominance over the systemic and local factors of host resistance. Infection is therefore a manifestation of a disturbed host/bacteria equilibrium in favour of the invading bacteria. This elicits a systemic septic response, and also inhibits the multiple processes involved in wound healing. Lastly, infection can result in a prolonged inflammatory phase and thus slow healing, or may cause further necrosis of the wound. The granulation phase of the healing process will begin only after the infection has subsided.

Chronically contaminated wounds all contain tissue bacterial flora. These bacteria may be indigenous to the patient or might be exogenous to the wound. Closure, or eventual healing of the wound is often based on a physician's ability to control the level of the bacterial flora.

If clinicians could respond to wound infection as early as possible the infection could be treated topically as opposed to having to use antibiotics. This would also lead to less clinical intervention/hospitalisation and would reduce the use of antibiotics and other complications of infection.

Current methods used to identify bacterial infection rely mainly on judgement of the odour and appearance of a wound. With experience, it is possible to identify an infection in a wound by certain chemical signs such as redness or pain. Some clinicians take swabs that are then cultured in the laboratory to identify specific organisms, but this technique takes time.

Pain is also associated with infected and chronic wounds. Biochemically, pain is experienced when there is an increase of kinins (bradykinin) in the area of the wound. Kinins are produced by the proteolytic breakdown of kininogen, and the protease responsible for this is kallikrein. Kallikrein also stimulates the production of tissue plasminogen activator (t-PA)

It is known to provide antimicrobial wound dressings. For example, such dressings are known having a liquid-permeable wound contacting layer, an intermediate absorbent layer and an outer, liquid-impervious backing layer, in which one or more of the layers contains an antimicrobial agent. For example, EP-A-0599589 describes layered wound dressings having a wound contacting layer of a macromolecular hydrocolloid, an absorbent layer, and a continuous, microporous sheet intermediate the wound contacting layer and the absorbent layer. The absorbent layer contains a low molecular weight antimicrobial agent that can diffuse into the wound.

Previous therapeutic (e.g. antimicrobial) wound dressings suffer from the drawback that the release of the therapeutic agent is relatively unresponsive to the condition of the wound being treated. This is undesirable because all unnecessary medication can interfere with the processes of wound healing. In the case of antimicrobial wound dressings, unnecessary medication can result in resistant microorganisms.

There is thus a need for a wound treatment device that will selectively release therapeutic agents such as antimicrobial agents and/or pain relieving agents into wounds only when there is a clinical need. Such a device could provide early intervention with suitable treatment (e.g. a topical antimicrobial treatment) before severe clinical symptoms or wound chronicity sets in.

In a first aspect, the present invention provides a wound treatment device comprising a water-impermeable envelope having at least one aperture, wherein the envelope contains a therapeutic substance, and wherein the at least one aperture in the envelope is blocked by a material that breaks down in the presence of one or more components of wound fluid thereby permitting the active substance to contact the wound fluid.

The term "envelope" refers to a small package or enclosure that can be inserted onto or into a wound. It is preferably covered by a secondary dressing to hold it in place and provide absorbency for wound fluid. The package is substantially impermeable to liquid water until the aperture is opened by the action of one or more components present in wound fluid. The envelope outside the aperture is normally formed from a material that is substantially impermeable to wound fluid, and that preferably does not break down in the presence of wound fluid. The wound fluid and/or the wound is thus not exposed to the therapeutic agent inside the envelope until the aperture is opened, and this enables the treatment to be tailored to predetermined wound conditions and unnecessary medication to be avoided. The device can be used in conjunction with a wide range of existing wound dressings, and is sufficiently small that it will not interfere with the absorbency of such dressings.

In certain embodiments the envelope is formed substantially from flexible sheet material. The sheet material is usually substantially water-impermeable (it may be permeable to water vapor, but not to liquid water), and suitably it is substantially non-degradable or erodible in wound fluid. In this way the walls of the envelope around the enclosure are substantially impermeable to, and unaffected by, the wound fluid. Preferably, the envelope consists essentially of such sheet material, such as thermoplastic film, for example in the form of a sachet. Typical film thicknesses are from about 10 to about 100 micrometers. Suitable thermoplastics include polyolefins such as polyethylene, copolymers such as ethylene methyl acrylate, or fluoropolymers such as polyvinylidene fluoride. Such envelopes are extremely low cost and can be made in a broad range of sizes and shapes enabling them to be applied to all types of wounds, including cavity wounds. Suitable sizes include envelopes having a maximum dimension of from about 2 mm to about 200 mm, for example from about 5 mm to about 100 mm, typically from about 10 mm to about 50 mm. Typical envelope configuration is a sachet formed by bonding together two sheets of film material (or one sheet folded over) around a periphery. Other suitable envelopes can be made from a web or tube of sheet material on form-fill-seal equipment.

Preferably, the aperture or apertures take up only a small part of the area of the envelope, since the barrier materials are generally more expensive than the sheet materials used to form the envelope. In certain embodiments, the total area of the apertures in the envelope is from about 0.01 to about 1 cm$^2$. Preferably, the envelope has fewer than 10 such apertures, more preferably fewer than 5, and most preferably only one such aperture. Typically, the apertures make up from about 0.1% to about 50% of the surface area of the envelope, more typically from about 1% to about 30%, and preferably from about 1% to about 10% of the surface area of the envelope.

The mean area of each aperture may for example be from about 1 to about 400 mm$^2$, preferably from about 2 to about 200 mm$^2$, and more preferably about 10 to about 100 mm$^2$.

The apertures in the envelope are blocked by a material that breaks down in wound fluid to open the apertures. The breakdown of the barrier material may be by dissolution, or by enzymatic or other chemical degradation by the ingredients of wound fluid. In certain embodiments, the barrier material breaks down preferentially in heavily exuding wounds. In certain embodiments, the degradable material breaks down preferentially in infected wounds.

For example, the barrier material may comprise a water soluble material, such as a water soluble macromolecule. At medium to high levels of exudate the soluble material is dissolved by the exudate, thus opening the apertures. At low levels of exudate or where there is a dry wound the soluble material will stay in place so that the apertures in the device remain occluded.

Suitable soluble materials for partially or completely occluding the apertures include water soluble macromolecular materials (hydrogels) such as sodium alginate, sodium hyaluronate, alginate derivatives such as the propylene glycol alginate described in EP-A-0613692, and soluble hydropolymers formed from vinyl alcohols, vinyl esters, vinyl ethers and carboxy vinyl monomers, meth(acrylic) acid, acrylamide, N-vinyl pyrrolidone, acylamidopropane sulphonic acid, PLURONIC (Registered Trade Mark) (block polyethylene glycol, block polypropylene glycol) polystyrene-, maleic acid, NN-dimethylacrylamide diacetone acrylamide, acryloyl morpholine, and mixtures thereof. Suitable hydrogels are also described in U.S. Pat. No. 5,352,508.

Other suitable materials for occluding the apertures of the device are polymeric materials that are not soluble in water, but that are bioerodible in wound fluid. Examples include polylactide/polyglycolide copolymers, oxidized regenerated cellulose, chitosan, chitin, and mixtures thereof.

Other suitable materials for partially or completely occluding the apertures of the envelope are pH-sensitive materials that are substantially insoluble in water at 25° C. under acidic conditions, but substantially soluble in water at 25° C. under neutral or alkaline conditions. Whilst it is no simple matter to determine the actual pH at a wound site, it appears that the pH of chronic or infected wounds is neutral or slightly alkaline, whereas the pH of intact skin is slightly acidic (pH 4 or 5).

Preferably, the pH-sensitive material is substantially insoluble in water at 25° C. and pH 4 and substantially soluble in water at 25° C. and pH 8. Preferably, the polymer becomes soluble with increasing pH at a pH in the range of 5 to 7, more preferably 5.5 to 6.5. In this context the term "soluble" preferably denotes an equilibrium solubility of the material greater than 1% w/w in water at 25° C. Particularly suitable are film-forming polymers and mixtures, such as those used to provide enteric coatings on orally administered medicaments.

Preferably, the pH-sensitive material comprises a polymer selected from the group consisting of cellulose derivatives, starch derivatives, pectins, polyacrylates, polyvinyl acetate phthalate, and mixtures thereof.

Preferred cellulose derivatives are selected from cellulose acetate phthalate, cellulose acetate trimellitate, hydroxypropyl methyl cellulose, hydroxypropyl methyl cellulose acetate succinate, carboxymethyl ethyl cellulose, oxidised regenerated cellulose, and mixtures thereof.

Preferred polyacrylates are selected from the copolymers of methacrylic acid with methyl methacrylate. Particularly preferred are various copolymers of this type sold under the Registered Trade Mark EUDRAGIT. By varying the ratio of methacrylic acid to methyl methacrylate it is possible to control the pH at which these copolymers dissolve in order to optimise the properties of the material.

In yet other embodiments, the degradable material occluding the aperture comprises a substrate for an enzyme present in wound fluid.

For example, it has been discovered that wound fluid from infected wounds, and from wounds that are apparently not clinically infected but which go on to become infected within a few days, have high levels of neutrophil elastase activity and may also have high levels of other inflammatory enzymes, such as macrophage proteases, other neutrophil proteases, bacterial collagenase, plasmin, hyaluronidase, kallikrein or t-PA. It is also known that the wound fluid produced by chronic wounds such as diabetic ulcers, decubitis ulcers or venous ulcers, have elevated levels of protease enzymes. Hence, the use of enzyme substrates enables the properties of the devices according to the present invention to be responsive selectively to wound infection and wound chronicity.

Preferred enzyme substrates for use in the degradable material comprise a substance selected from the group consisting of elastin, fibronectin, collagen, crosslinked gelatin, fibrinogen, casein, hyaluronic acid, plasminogen, fibrin, chitin, chitosan, oxidized cellulose, polylactide/polyglycolide copolymers, and mixtures thereof.

In preferred embodiments, the materials for partially or completely occluding the apertures of the envelope comprise substrate materials for one or more protease enzymes present in wound fluid, especially infected wound fluid. Such proteases include elastase, collagenase, pectinase, matrix metalloproteinases, and mixtures thereof. Preferred substrate materials include substances selected from the group consisting of elastin, fibronectin, collagen, crosslinked gelatin, fibrinogen, casein, hyaluronic acid, plasminogen, fibrin, and mixtures thereof.

The barrier composition may comprise at least 25%, more preferably at least 50% w/w based on the weight of the composition of the soluble macromolecular materials, ph-sensitive materials, or substrate materials on a dry weight basis. The barrier composition may further comprise from about 5 to about 50% by weight, preferably from 15 to 40% by weight, on the same basis of one or more humectants and/or plasticisers such as glycerol, sorbitol or polyethylene glycol.

The one or more therapeutic agents may be any substance suitable for the treatment of wounds. In certain embodiments the therapeutic agents are selected from the group consisting of antiseptics, antibiotics, analgesics, steroids and growth factors. Preferred therapeutic agents are antimicrobial agents including metallic silver, silver salts and compounds such as silver sulfadiazine, povidone iodine, chlorhexidine and mixtures thereof, and analgesic agents including benzocaine, lidocaine and mixtures thereof.

The therapeutic agent may be present in the envelope in particulate or soluble or otherwise dispersible form, so that it can pass out of the envelope into the wound once the aperture is opened by the action of wound fluid. In other embodiments, the therapeutic agent may be retained inside the envelope even after the aperture has opened, for example by being dispersed in or on a substrate that is too large to fit through the aperture. An example would be a silver treated cloth.

In certain embodiments the therapeutic material inside the envelope is adapted to provide sustained release of the therapeutic agent in wound fluid. For example, the material may comprise a bioerodible substance having the therapeutic agents dispersed or encapsulated therein. Suitable bioerodible substances include proteins such as albumin, collagen, cross-linked gelatin or zein, polysaccharides such as oxidized regenerated cellulose, biodegradable synthetic polymers such as polylactate/polyglycolate copolymers, glycosaminoglycans such as hyaluronate, and mixtures thereof.

In certain embodiments, the therapeutic material may be dispersed in or on particles suitable for drug delivery. The particles may be made by any suitable technique, including comminution, coacervation, or two-phase systems for example as described in U.S. Pat. No. 3,886,084. Techniques for the preparation of medicated microspheres for drug delivery are reviewed, for example, in *Polymeric Nanoparticles and Microspheres*, Guiot and Couvreur eds., CRC Press (1986). The microparticles are preferably loaded with from 1 to 90 wt. %, more preferably from 3 to 50 wt. % of the therapeutic agents.

Preferably, the wound treatment device according to the present invention is sterile and packaged in a microorganism-impermeable container.

In a second aspect, the present invention provides a wound dressing comprising a wound treatment device according to the present invention.

In a third aspect, the present invention provides a method of treatment of a wound comprising applying thereto a device according to the present invention. Preferably, the method further comprises applying a wound dressing over the device.

Figure 2:
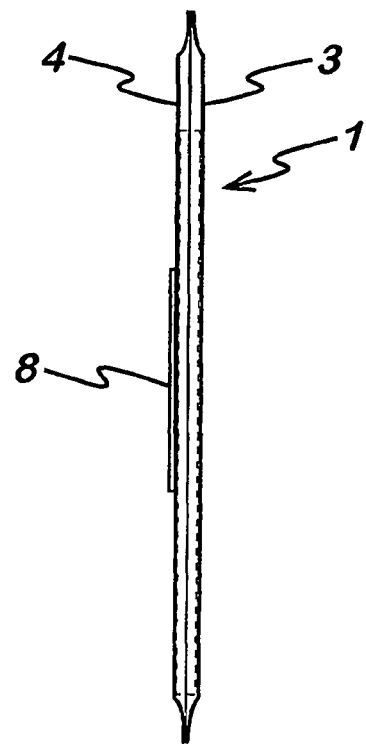

An embodiment of the present invention will now be described further, by way of example, with reference to the accompanying drawings, in which:

FIG. 1 shows a perspective view partially cut away of a wound treatment device according to the invention; and FIG. 2 shows a longitudinal cross-sectional view of the dressing of FIG. 1.

EXAMPLE 1

Referring to FIG. 1, the wound treatment article 1 comprises an envelope 2 of substantially liquid-impermeable sheet material. The envelope consists of front and back faces 3,4 of a continuous polypropylene film that are heat bonded around their and edge margin 5 to form a waterproof sachet. Inside the envelope there is a rectangular sheet 6 of silver-impregnated antimicrobial cloth. The envelope comprises an aperture 7 occluded by a collagenase-degradable film composition 8

The device is prepared as follows. 1 g of collagen fibers formed by freeze drying Type I collagen extracted from limed bovine hide were suspended in 100 ml of 0.05M acetic acid. This suspension was poured into a plastic dish to a thickness of 4 mm. The dish was placed in a drying cabinet at room temperature until the weight of the suspension had reduced to 50% of the initial weight. At this stage the apertured polymer sheet that will form the apertured face 3 of the envelope was placed on the surface of the collagen suspension. The suspension was then fully dried and peeled from the square dish. The resulting material has the aperture of the sheet occluded by a thin film of Type I collagen. The apertured sheet 3 with the layer of collagen 8 applied thereto was then assembled into the device by heat bonding to the back sheet 4, with the antimicrobial cloth inserted between the sheets 3 and 4.

The device is packaged in a microorganism-impermeable pouch (not shown), and sterilised using gamma radiation.

In use, the device 1 is removed from the package, and the article is applied to the wound and held in place by a sterile and absorbent secondary dressing. The dissolution of the collagen contained in the barrier layer 8 in the presence of elevated levels of collagenase exposes the wound fluid to the antimicrobial silver cloth inside the envelope in response to increased collagenase production by infected or chronic wounds.

EXAMPLE 2

In another embodiment, the barrier layer 8 contained chitosan as the biodegradable component. The chitosan containing film composition prepared as follows.

100.0 grams of chitosan chloride was mixed in 1.5 liters of water until blended. 200.0 grams of glycerol were blended into the mixture, after which 200.0 grams of polyethylene glycol ("PEG") were then added. The resulting mixture was then filtered and coated over the aperture as described in Example 1. The mixture was then frozen and freeze dried, or air dried in circulating air at room temperature.

The above embodiments have been described by way of example only. Many other embodiments falling within the scope of the accompanying claims will be apparent to the skilled reader.

The invention claimed is:

1. A wound treatment device comprising a water-impermeable envelope having one aperture, wherein the envelope contains a therapeutic agent, wherein the one aperture in the envelope is blocked by a degradable material that breaks down in the presence of one or more components of wound fluid thereby permitting the therapeutic agent to contact the wound fluid, wherein the total area of the aperture in the envelope is from about 0.01 to about 1 $cm^2$, wherein the therapeutic agent is dispersed in or on a substrate larger than the total area of the aperture, wherein the therapeutic agent is retained inside the envelope after the aperture is opened, and wherein no part of the therapeutic agent contacts the wound surface.

2. A wound treatment device according to claim 1, wherein the therapeutic agent is selected from the group consisting of antiseptics, antibiotics, analgesics, steroids and growth factors, and mixtures thereof.

3. A wound treatment device according to claim 2, wherein the therapeutic agent is dispersed or encapsulated in a bioerodible substance.

4. A wound treatment device according to claim 3, wherein the bioerodible substance is selected from the group consisting of proteins, polysaccharides, biodegradable synthetic polymers, glycosaminoglycans, and mixtures thereof.

5. A wound treatment device according to claim 2, wherein the therapeutic agent comprises an antimicrobial agent selected from colloidal silver, silver sulfadiazine, povidone iodine, chlorhexidine, and mixtures thereof.

6. A wound treatment device according to claim 2, wherein the therapeutic substance is dispersed in or on a solid substrate.

7. A wound treatment device according to claim 2, which is sterile and packaged in a microorganism-impermeable container.

8. A wound treatment device according to claim 1, wherein the degradable material comprises a substrate for an enzyme present in wound fluid.

9. A wound treatment device according to claim 8, wherein the degradable material comprises a substance selected from the group consisting of elastin, fibronectin, collagen, crosslinked gelatin, fibrinogen, casein, hyaluronates, plasminogen, fibrin, chitin, chitosan, oxidized cellulose, polylactide/polyglycolide copolymers, and mixtures thereof.

10. A wound treatment device according to claim 1, wherein the envelope is formed substantially from flexible sheet material.

11. A wound treatment device according to claim 1, wherein the degradable material breaks down preferentially in infected wounds.

12. A wound dressing comprising a wound treatment device according to claim 1.

* * * * *